(12) United States Patent
Bradford et al.

(10) Patent No.: US 11,291,085 B1
(45) Date of Patent: Mar. 29, 2022

(54) INDUCTION OVEN WITH SELECTABLE RESONANCE FREQUENCY

(71) Applicants: Daniel Bradford, North Las Vegas, NV (US); Jason Viggato, Las Vegas, NV (US)

(72) Inventors: Daniel Bradford, North Las Vegas, NV (US); Jason Viggato, Las Vegas, NV (US)

( * ) Notice: Subject to any disclaimer, the term of this patent is extended or adjusted under 35 U.S.C. 154(b) by 0 days.

(21) Appl. No.: 17/323,802

(22) Filed: May 18, 2021

(51) Int. Cl.
| | |
|---|---|
| *H05B 6/64* | (2006.01) |
| *H05B 6/06* | (2006.01) |
| *H05B 6/10* | (2006.01) |
| *H05B 6/36* | (2006.01) |
| *F27B 17/02* | (2006.01) |
| *F27D 7/04* | (2006.01) |
| *A61L 2/06* | (2006.01) |
| *A61L 2/24* | (2006.01) |

(52) U.S. Cl.
CPC ............ *H05B 6/06* (2013.01); *A61L 2/06* (2013.01); *A61L 2/24* (2013.01); *F27B 17/02* (2013.01); *F27D 7/04* (2013.01); *H05B 6/105* (2013.01); *H05B 6/362* (2013.01); *A61L 2202/11* (2013.01); *A61L 2202/122* (2013.01); *A61L 2202/14* (2013.01); *A61L 2202/182* (2013.01); *F27D 2007/045* (2013.01)

(58) Field of Classification Search
CPC ......... H05B 6/44; H05B 6/129; A61L 2/0064; A61L 2/12
USPC ................ 422/21–22, 186, 307; 219/759
See application file for complete search history.

(56) References Cited

U.S. PATENT DOCUMENTS

| | | |
|---|---|---|
| 5,552,112 A | 9/1996 | Schiffmann et al. |
| 2002/0088111 A1 | 7/2002 | Von Arx et al. |
| 2011/0211989 A1* | 9/2011 | Hemphill .......... A61L 2/06 422/22 |
| 2017/0118805 A1 | 4/2017 | Ha et al. |

FOREIGN PATENT DOCUMENTS

CN 209575340 11/2019

* cited by examiner

*Primary Examiner* — Monzer R Chorbaji
(74) *Attorney, Agent, or Firm* — Jeffrey G. Sheldon; Andrew Naglestad; Cislo & Thomas LLP (57) ABSTRACT

An induction oven for the sterilization of equipment is disclosed. The invention effectively reduces sterilization cycle times from 90 minutes to less than 30 minutes using dry heat. In addition to increased efficiency, the dry heat also avoids pitting and other forms of degradation of the materials being sterilized. The oven can be configured by the user to generate a resonance of a particular frequency to target the specific type of metal or other induction material being heated. Target induction materials include cast iron, stainless steel, brass, and graphite, for example. The oven includes a coil that generates the time-varying electromagnetic field using a two-dimensional spiral having a rectangular pattern. The spiral coil is formed on a printed circuit board. The oven is configured to receive a container for heating articles. The container includes a bin, e.g., aluminum, and transparent lid with a gasket therebetween to produce an airtight seal. The container can be used to both sterilize equipment as well as store the sterilized equipment without contamination.

17 Claims, 6 Drawing Sheets

INDUCTION OVEN WITH SELECTABLE RESONANCE FREQUENCY

TECHNICAL FIELD

The invention generally relates to an induction oven. In particular, the invention pertains to an induction oven with a selectable resonance frequency and airtight container for heating articles.

BACKGROUND

Hospitals commonly use autoclaves to sterilize articles such as surgical instruments and other medical equipment. Proper sterilization is of vital importance to ensure complete destruction of microorganisms and eliminate health hazards to subsequent patients. Autoclaves typically use steam for sterilization of steel and other heat resistant materials. The process of generating steam and killing various pathogens with steam is time consuming because it requires the heating of water, the heating of the instruments, and then the cooling of those instruments after sterilization. The combination of steam and exposure time, can also produce pitting and other forms of corrosion of metals. There is therefore a need for a technique for quickly sterilizing equipment without also damaging that equipment in the sterilization process.

SUMMARY

The invention in the preferred embodiment features a novel induction oven for the sterilization of medical equipment or other application. The invention effectively reduces sterilization cycle times from 90 minutes to less than 30 minutes while avoiding pitting and other forms of degradation of the materials being sterilized. In addition, the induction oven requires less energy than an autoclave, is less expensive to install since it operates on single phase power rather than a three-phase electrical service, and is safer since it operates at atmospheric pressure.

In one exemplary embodiment, the invention is an oven comprising a cabinet and removable sterilization container. The cabinet comprises a user interface, power supply, and tank circuit. The user interface is configured to receive a user's metal type or frequency selection, each selection being tailored for one of a plurality of metal types or other induction material types. The power supply is configured to generate an alternating current with an output frequency corresponding to the metal type selected by the user. The tank circuit includes a tank capacitor and an inductive heating coil driven by the power supply. In the preferred embodiment, the inductive heating coil is a copper trace etched from a printed circuit board. The shape of the inductive heating coil is a two-dimensional pattern in the form of a spiral, preferably a rectangular spiral with a plurality of loops. Each of the loops can be formed from four straight segments of copper about 0.25 inches wide and 0.012 inches thick.

The container for heating articles includes a bin and lid with a hermetic seal therebetween such as an elastomeric gasket interposed between them. Spring clips around the circumference of the bin are detachably connected to the lid. When connected, the spring clips apply a downward force on the lid which produces a hermetic seal therebetween. The seal is only broken when the clips are detached from lid. As such, the container serves as a storage device for any objects being sanitized during and after the sanitization process. Since the container is removable from the cabinet portion of the oven, the container can be used as a long-term storage device for sterilized items without jeopardizing the sterility of those items. For maximal utility, the lid is made from a translucent or transparent material to enable the user to visually inspect the contents of the container without breaking the hermetic seal or introducing outside contamination.

BRIEF DESCRIPTION OF DRAWINGS

The present invention is illustrated by way of example and not limitation in the figures of the accompanying drawings, and in which.

DETAILED DESCRIPTION OF THE INVENTION

The preferred embodiment of the present invention includes an induction oven configured to quickly generate heat to sterilize articles including medical instruments such as surgical instruments, for example. The heat is generated by a time-varying electromagnetic field without the need for water or steam. Using the present invention, sterilization cycles are completed quickly and efficiently without any damage to the instruments being sterilized.

Figure 1:
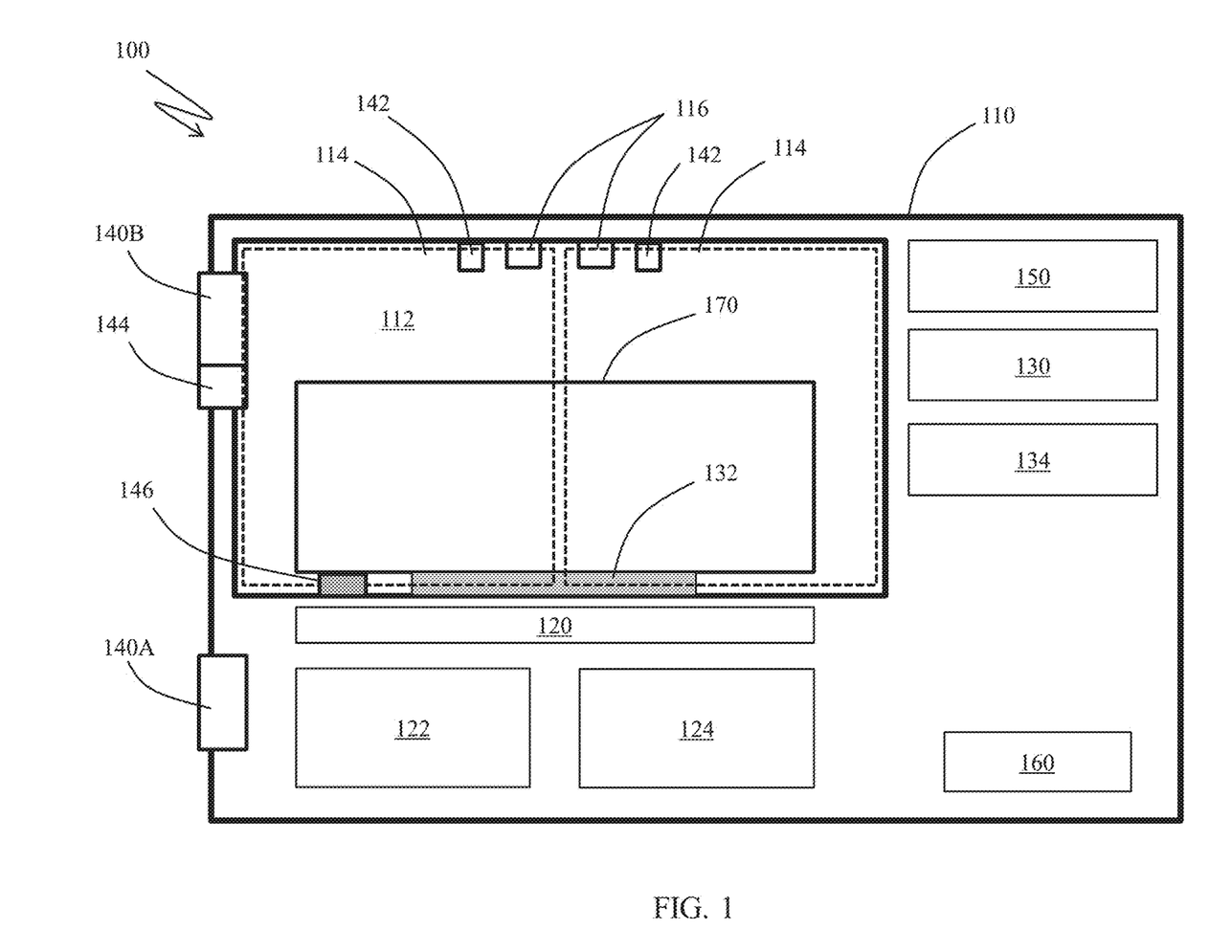
FIG. 1 is a diagrammatic illustration of an induction oven, in accordance with a preferred embodiment of the present invention.

As illustrated in FIG. 1, the preferred embodiment of the oven 100 generally includes a cabinet 110 and a container 170 configured to hold and heat surgical instruments in the cabinet during and after the sterilization process. The container 170 is discussed in more detail below. The cabinet 110 in the preferred embodiment includes an oven compartment 112 and a pair of doors 114, which are constructed from stainless steel and high-temperature insulation in the walls of the cabinet and doors. The doors 114 are secured to the cabinet by means of a rotary door latch system 116 that drives two rods (not shown), one up and one down, into corresponding holes (not shown) in the cabinet when locked.

The cabinet 110 further includes the following components: an inductive heating coil 120, a heating circuit 122, an analog output module 124, a microcontroller 130, at least one temperature sensor 132, a temperature sensor signal conditioning circuit 134, a plurality of cooling fans 140A, 140B, contact closure sensors 142, a user interface 150 with display, and data interface 160.

The inductive heating coil 120 in the preferred embodiment is a printed circuit board (PCB) with an embedded copper coil. The coil, preferably a spiral pattern, generates the time-varying electromagnetic field that produces currents in the container and/or instruments therein. The inductive heating coil 120 is discussed in greater detail below.

The heating circuit 122 is configured to accept 120 or 220 volts alternating current (AC) and supply high-frequency AC current to the inductive heating coil. The heating circuit 122 is discussed in more detail below in context of FIG. 2.

In the preferred embodiment, the analog output module 124 is an analog circuit configured to output a voltage signal between zero and ten volts to the power supply. The analog output circuitry comprises a low-pass filter, preferably a Butterworth filter, configured to condition the output signal and produce a direct current (DC) voltage.

The microcontroller 130 is a digital microprocessor configured to execute control algorithms necessary to interpret user input, interpret input signals from one or more sensors in the cabinet 110, implement a sanitization cycle, and monitor various inputs to ensure that the sanitization cycle has completed successfully.

The temperature sensor 132 is configured to detect the temperature at the base of the container 170. The sensor 132 can include a signal conditioning circuit 134 configured to suppress noise generated by the inductive heater coil. In the preferred embodiment, this signal conditioning circuit 134 includes a Wheatstone bridge with built-in gain and ferrite beads.

The cabinet 110 includes a pair of cooling fans 140A, 140B controlled by the microcontroller 130. A first cooling fan 140A is configured to pass air over the inductive heating coil 120 to prevent damage due to overheating. This fan is powered on as soon as the logic has confirmed that all pre-start conditions have been met. One of the pre-start conditions is that the doors 114 be properly closed and secured with the rotary door latch system 116, for example. As soon as this is verified, the cooling fan 140A starts. In some embodiments, there is an air flow switch 144 configured to detect whether or not the first fan 140A is running. This indication can be a prerequisite for the initiation of any heating cycle. The second fan 140B is configured to cool the container 110 after the heating cycle is complete.

The contact closure sensors 142 are configured to detect the position of the oven doors 114, specifically whether the doors are properly closed and the rotary door latch system 116 engaged. The sensors 142 are located in the frame of the cabinet 110. When the doors 114 are closed, they press on the sensors 142 and cause closure of contacts to detect and confirm that the doors are secure. When the doors 114 are properly closed, the contact closure sensors 142 are configured to transmit a signal to the microcontroller 130.

The user interface 150 in the preferred embodiment includes a touch-sensitive liquid crystal display (LCD), for example, coupled to the microcontroller 130. The display 150 is configured to receive operational commands from the user and communicate the status of operational states to the user. In the preferred embodiment, the set of operational states includes a metal-type selection command. Using this command, the user selects the type of metal being sanitized in the oven 100, which corresponds to a particular frequency range at which the oven operates. Each frequency corresponds to one of a plurality of different types of metal. The operational frequencies are configured to maximize the power transmitted to the objects being sanitized, thereby minimizing the time necessary for the oven to complete its sanitization cycle of that metal. There is an operational frequency for stainless steel between 1 and 30 kHz, another frequency for mild steel and cast iron between 4 and 70 kHz, and another frequency for brass between 60 Hz and 10 kHz. The appropriate setting is determined by the user based on the type of articles being sanitized in the oven 100.

The data interface 160 is configured to exchange data between the microcontroller 130 and an external device or network. The data interface 160 can be configured to upload software to the microcontroller 130, or output operational/diagnostic data to a user device, for example. The data interface 160 may be a RS-232 level shifter chip, serial port, WiFi antenna, or BLUETOOTH™ antenna, with support circuitry, for example.

Figure 2:
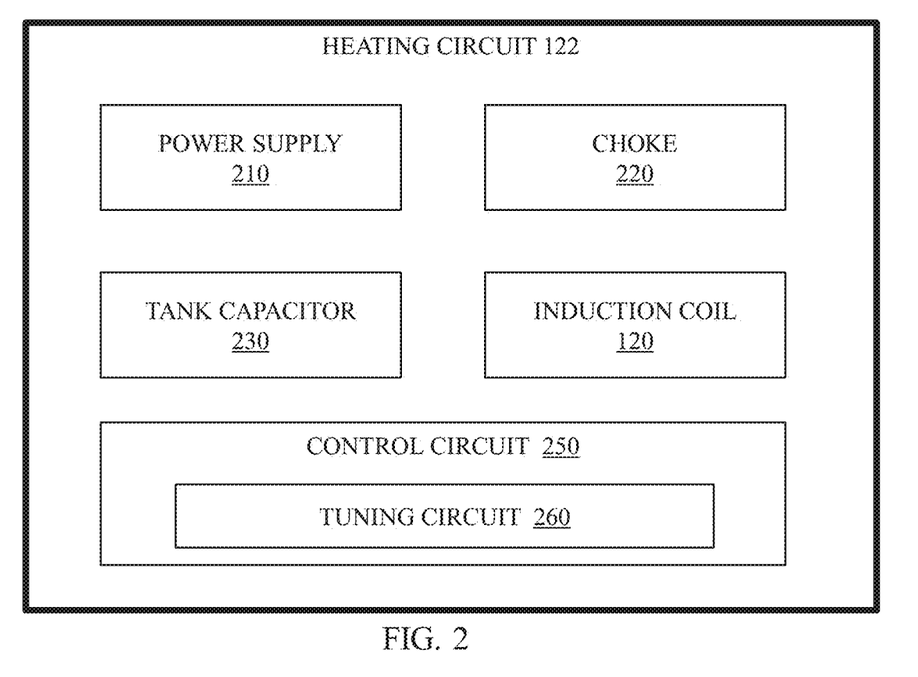
FIG. 2 is a functional block diagram of a heating circuit, in accordance with a preferred embodiment of the present invention.

As illustrated in FIG. 2, is the heating circuit in accordance with a preferred embodiment. The heating circuit 122 includes high-power components necessary to produce an electromagnetic field needed to elevate the temperature of multiple pounds of articles, such as medical instruments, to a temperature in excess of 300 degrees Fahrenheit. The heating circuit 122 includes a power supply 210, choke 220, tank capacitor 230, induction coil 120, and control circuit 250 with tuning circuit 260.

The power supply 210 is configured to convert 120 volt line voltage into alternating current with an output frequency of 1,000 hertz to 70,000 hertz.

The choke 220 is configured to serve as an inductor. The choke also serves as a filtering device to minimize the amount of AC frequency feedback to the 120 volt line voltage.

The tank capacitor 230 is connected to the inductive heating coil 120. Together, they operate as a resonance tank circuit. The resonance, in turn, energizes the coil 120 to induce the eddy currents in the objects being heated and/or sanitized.

The control circuit 250 is configured to monitor and regulate the amount of energy being generated by the coil 120 and the amount of power consumed by the oven. The link between the object being heated and the control circuit is the temperature sensor or temperature probe. The inductive heating coil then generates a time-varying magnetic field with an intensity that is based on the current resonating in the tank circuit. This field, in turn, creates eddy currents or resonant frequency vibrations in the object being heated. The coil has been designed to heat inductive materials—iron compounds, stainless steel, brass, graphite, etc.—depending on an operational mode selected by the user. The inductive heating coil 120 is discussed in more detail below.

The tuning circuit 260 includes a tuning circuit configured to modify the frequency at which the tank circuit resonates. To target cast iron, for example, the tuning circuit drives the tank circuit to operate at a frequency of 4 kHz and 70 kHz. To target stainless steel, the tuning circuit drives the tank circuit to operate at a frequency of 1 kHz to 30 kHz. Additional target frequencies may be implemented to target other materials.

In some embodiments, the cabinet 110 includes one or more proof switches 146 positioned in the oven compartment 112 under the container 170. When a container 170 is placed in position above the inductive heating coil 120, the container 170 depresses the proof switch 146. This is to ensure that the container is physically in the cabinet 110 before the coil 120 is energized. The coil 120 cannot be energized if one or more containers 170 are not in position in the cabinet 110.

Figure 3:
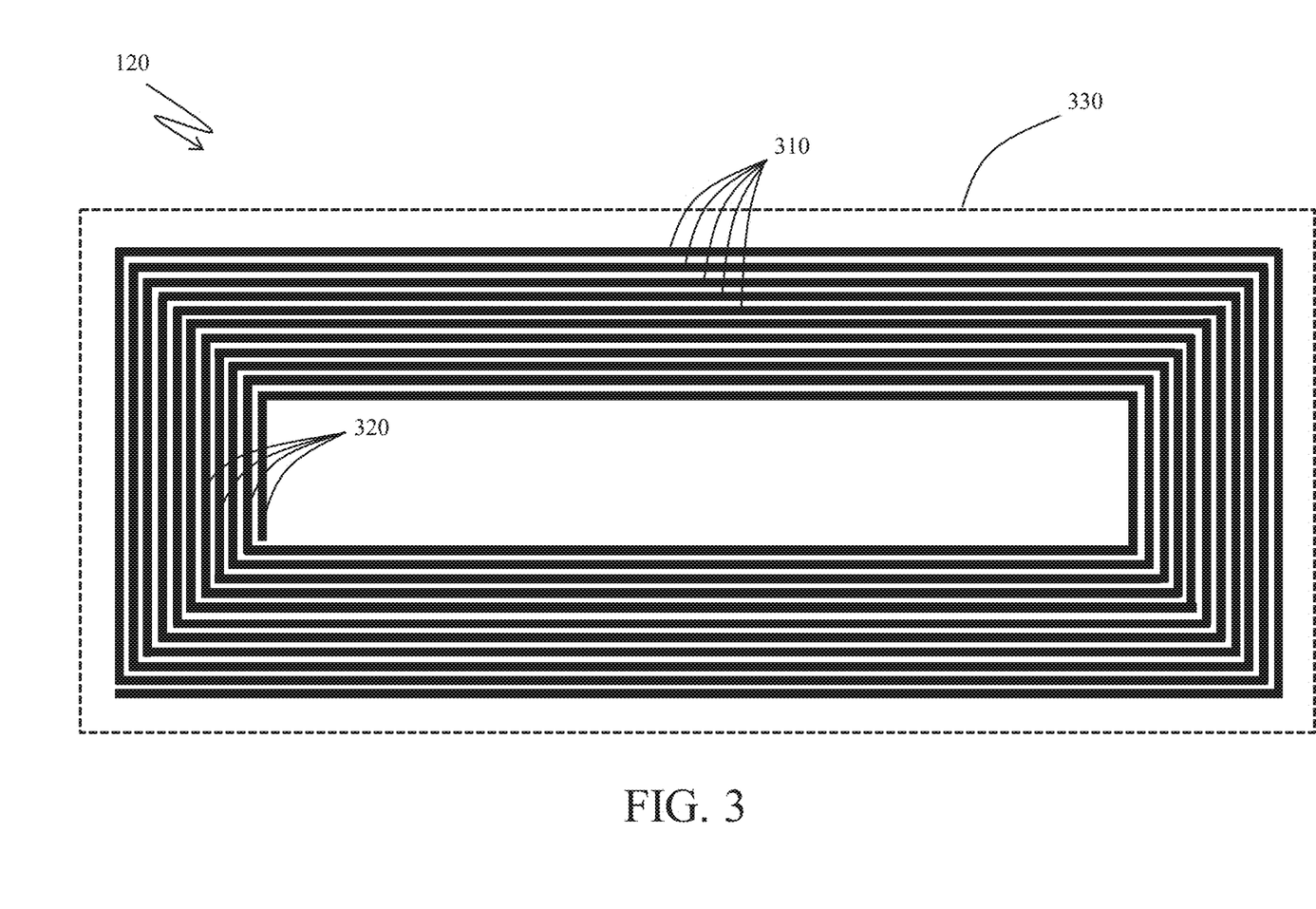
FIG. 3 is a spiral coil formed on a printed circuit board, in accordance with a preferred embodiment of the present invention.

Illustrated in FIG. 3 is the induction coil of the preferred embodiment of the present invention. The inductive heating coil 120 comprises a plurality of copper loops, each loop comprising a plurality of strips or segments 310, 320 affixed to a sheet of fiber-embedded plastic to form a rigid circuit board 330. The copper segments that generate the energy field are affixed to the underside of the board. The copper segments form a spiral pattern in a two-dimensional plane. The spiral pattern includes a plurality of rectangles that wind around a single center point, each rectangle characterized by a diagonal having a different length. The length of the diagonal of the rectangles steadily increases as the spiral widens (or decreases as the spiral tightens). In the preferred embodiment, the rectangles comprise numerous straight segments 310, 320 of copper. In the preferred embodiment, there are approximately eleven complete loops, one nested inside the other. The inner-most rectangular loop is approximately 22 inches wide and 3.75 inches deep.

The width of the copper segments 310, 320 and the spacing therebetween produces a specific range of frequencies designed to affect the target material in the container 170. In the preferred embodiment, the straight segments 310, 320 of copper are 0.25 inches wide and 0.012 inches thick with a gap of 0.125 inches between adjacent segments running parallel to one another.

Figure 4:
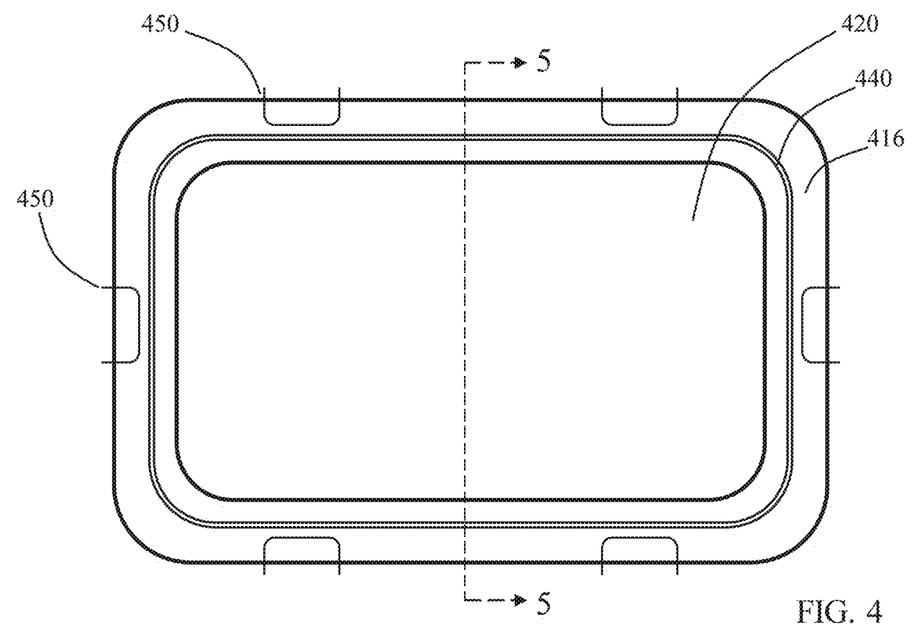
FIG. 4 is a top view of a container for heating articles, in accordance with a preferred embodiment of the present invention.
Figure 5:
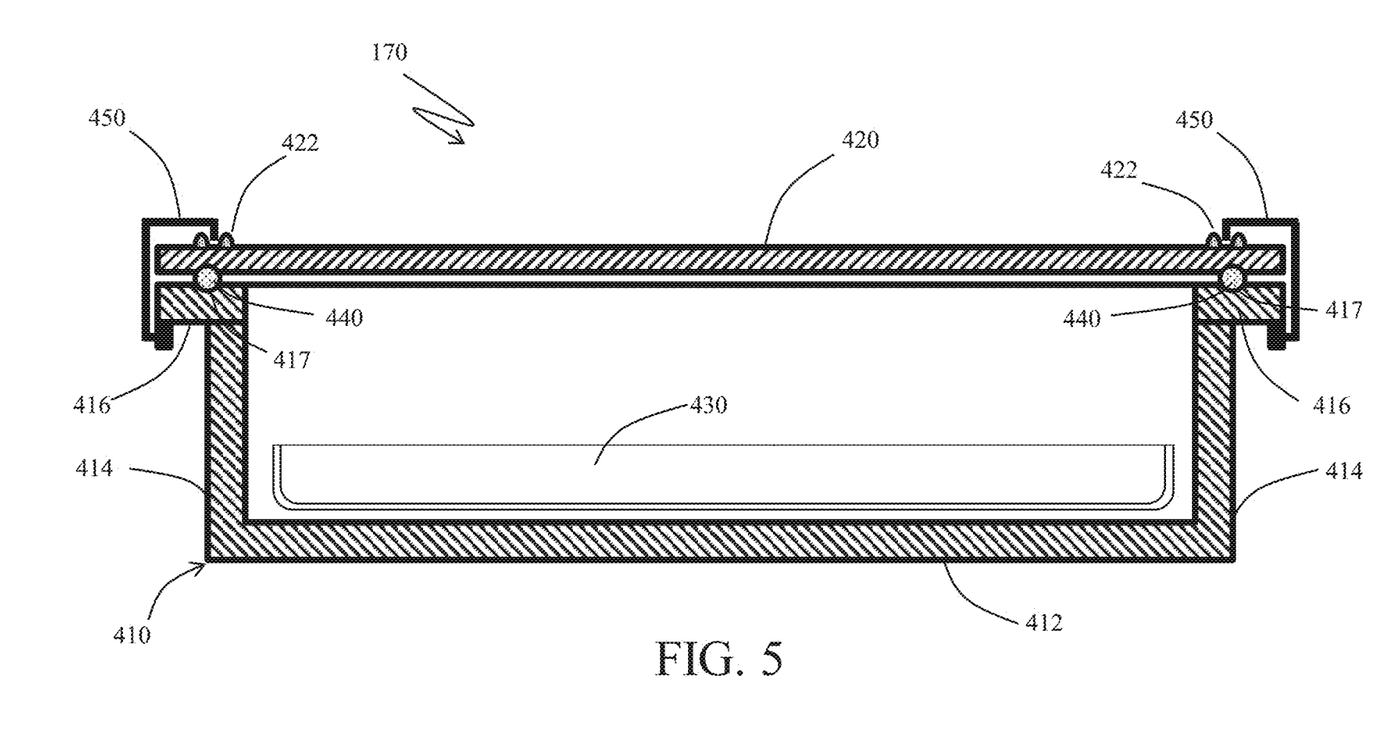
FIG. 5 is a cross section of a container for heating articles, in accordance with a preferred embodiment of the present invention.

The preferred embodiment of the container 170 is shown in plan view in FIG. 4 and in cross section in FIG. 5. In the preferred embodiment, the container 170 includes a bin 410, a transparent or translucent acrylic lid 420, and an optional plastic dish 430. The bin 410 preferably is made of aluminum to increase heat dissipation after the sterilization process is complete. The bottom surface 412 of the aluminum bin includes an iron coating to increase the energy emitted by the coil and absorbed by the container. The bin further includes a powder coating, i.e., heat-hardened paint, applied to the inside of the bin to seal any rough surface and provide improved sanitation.

The bin 410 includes four walls 414 and a continuous horizontal flange 416 that caps each of the walls. The flange 416 includes a groove 417 configured to receive a TEFLON™ or other elastomeric gasket 440. When the lid 420 is secured to the bin 410, the gasket 440 provides an airtight seal.

In the preferred embodiment, the container 170 includes six spring clips 450 mounted to the side walls 414 of the bin 410. The spring clips 450 are configured to rotate from the sides of the bin 410 to a point of contact on the upper side of the clear acrylic lid 420. The clips 450 then hold the lid 420 down against the gasket 440 to create a hermetic seal between the lid and bin.

In the preferred embodiment, the container 170 is ten inches wide by fourteen inches long by two inches deep. Other bins can be 20 inches wide by 14 inches long, or 30 inches wide by 14 inches long.

The lid 420 can be injection molded from clear acrylic. This permits visual inspection of the contents of the bin 410 without removing the lid 420, thereby maintaining the sterility of the contents.

The lid 420 has a groove on its underside. This groove coincides with the groove in the horizontal flange 416 of the bin 410. The upper side of the lid includes six ridges 422 that align with the spring clips 450 on the bin 410. When the spring clips 450 reach over the lid 320, the ridges 422 provide a restraint for the clip to help hold its contact point with the lid 420 directly over the ridge. When properly restrained, the spring clips 450 apply a force that pulls the lid down onto the Teflon gasket 440 to create a seal. This seal prevents contamination from coming in contact with medical instruments after they are sanitized. Unless the clips are removed and the seal broken, the contents of the container 170 may remain sterile while in the container for an extended, if not indefinite, period of time.

In some embodiments, the container 170 includes a high-temperature nylon plastic tray 430 configured to hold the medical instruments or other items or articles being sterilized. The tray 430 provides separation between items and prevents them from rubbing against each other or against the bottom of the bin 410. The tray 430 protects the sharp edges from coming in contact with any other object to ensure that no damage occurs during the sterilization process. Each set of items being sterilized in the system may require new types of trays to be designed to hold them. In the preferred embodiment, the tray 430 is configured to receive, for example, dental instruments or surgical instruments.

Figure 6:
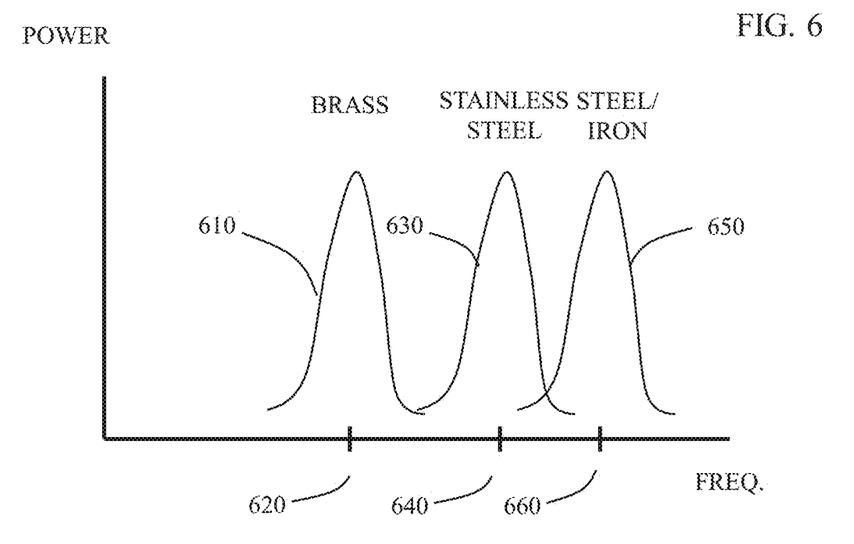
FIG. 6 is a frequency profile of peaks targeting different metal types or other induction material types, in accordance with a preferred embodiment of the present invention.

Illustrated in FIG. 6 is a spectral profile showing the center frequency and bandwidth of the frequencies used to target different materials. As shown, a first peak 610 with a first center frequency 620 is used to target brass. A second peak 630 with a second center frequency 640 is used to target stainless steel. A third peak 650 with a third center frequency is used to target mild steel and iron, for example. Additional frequencies may be used to specifically target graphite and other semiconductors, for example.

Figure 7:
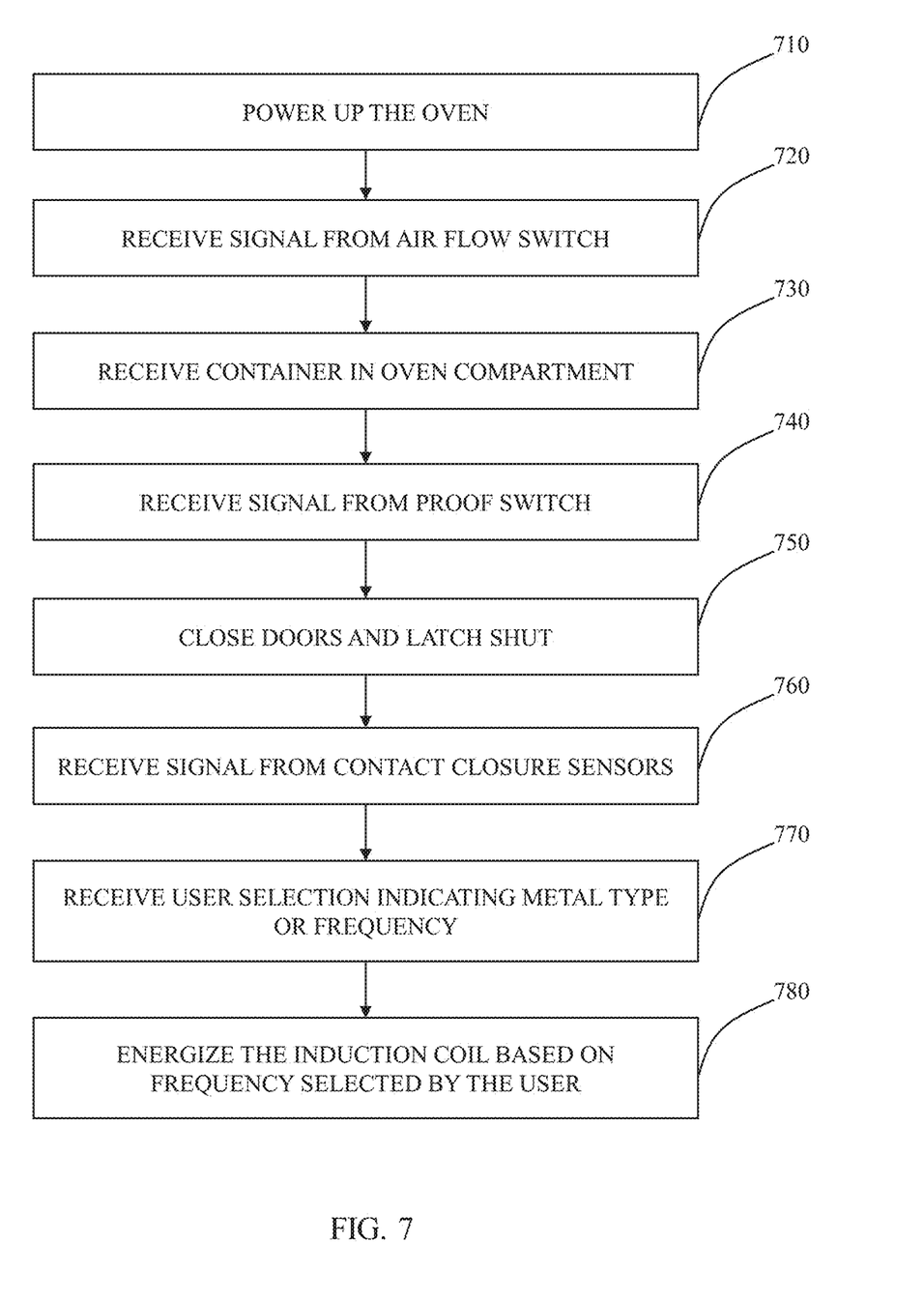
FIG. 7 is a flowchart of the process of energizing an induction coil for a metal type selected by a user, in accordance with a preferred embodiment of the present invention.

Illustrated in FIG. 7 is a flowchart of the process of energizing an induction coil for a metal type selected by a user. To start, the user powers up 710 the oven with the user interface 150 or dedicated button or toggle. When the oven 100 is powered up and the logic functions initiated, the first cooling fan 140A automatically turns on and the airflow confirmed by the air flow switch 144. The air flow switch 144 transmits 720 a signal confirming the presence of airflow to the microcontroller 130. The user also inserts 730 a container 170 with medical instruments or other articles to be heated 730 into the oven compartment. The weight of the container depresses the proof switch 146 and a signal transmitted 740 to the microcontroller 130 to confirm the presence of container. With the container in the oven, the user closes and locks the doors 114 by means of a rotary door latch system 116. The contact closure sensors 142 confirm that the doors are closed 750 and transmit 760 a signal to the microcontroller 130. The user then selects 770 various operational parameters including the metal type to be sanitized and/or the frequency of the electromagnetic radiation to be induced. If and when the microcontroller 130 verifies that (a) the air flow switch 144 detects airflow, (b) the proof switch 146 detects a container 170, and (c) the contact closure sensors 142 detect the doors closed, then the microcontroller energizes the heating circuit which causes the induction coil to generate 780 an electromagnetic wave at the frequency or frequency range selected by the user.

One or more embodiments of the present invention may be implemented with one or more computer readable media, wherein each medium may be configured to include thereon data or computer executable instructions for manipulating data. The computer executable instructions include data structures, objects, programs, routines, or other program modules that may be accessed by a processing system, such as one associated with a general-purpose computer or processor capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. Examples of mass storage devices incorporating computer readable media include hard disk drives, magnetic disk drives, tape drives, optical disk drives, and solid state memory chips, for example. The term processor as used herein refers to a number of processing devices including personal computing devices, servers, general purpose computers, special purpose computers, application-specific integrated circuit (ASIC), and digital/analog circuits with discrete components, for example.

Although the description above contains many specifications, these should not be construed as limiting the scope of the invention but as merely providing illustrations of some of the presently preferred embodiments of this invention.

Therefore, the invention has been disclosed by way of example and not limitation, and reference should be made to the following claims to determine the scope of the present invention.

What is claimed is:

1. An oven comprising:
   a user interface configured to receive a user selection, the user selection associated with one of a plurality of induction material types;
   a power supply configured to generate an alternating current with an output frequency corresponding to the user selection;
   a resonating tank circuit connected to the power supply, wherein the tank circuit comprises a tank capacitor and an inductive heating coil for generating an electromagnetic field, the inductive heating coil comprising a printed circuit board; and
   a container for containing an article to be sterilized, the container comprising a bin and lid with a hermetic seal therebetween;
   wherein the electromagnetic field produces a current in the container or an article in the container or both for sterilizing the article.

2. The oven of claim 1, wherein the output frequency is between 5,000 hertz and 50,000 hertz.

3. The oven of claim 2, wherein the inductive heating coil is a two-dimensional copper spiral.

4. The oven of claim 3, wherein the spiral is a rectangular spiral.

5. The oven of claim 4, wherein the rectangular spiral comprises a plurality of loops, each loop comprising a plurality of straight segments of copper.

6. The oven of claim 5, wherein the plurality of segments of copper are about 0.25 inches wide and 0.012 inches thick.

7. The oven of claim 3, wherein the bin is composed of aluminum.

8. The oven of claim 7, wherein the lid is composed of a transparent material.

9. The oven of claim 8, wherein the hermetic seal comprises an elastomeric gasket and clips, wherein the gasket is interposed between the bin and lid, and the clips are configured to press the bin and lid together.

10. An oven comprising:
    a user interface configured to receive a user selection, the user selection associated with one of a plurality of induction material types, wherein the plurality of induction material types include cast iron and stainless steel;
    a microcontroller;
    a power supply connected to the microcontroller, wherein the power supply is configured to generate an alternating current with an output frequency corresponding to the user selection;
    a resonating tank circuit connected to the power supply, wherein the tank circuit comprises a tank capacitor and an inductive heating coil; wherein the inductive heating coil comprises a printed circuit board with a rectangular spiral pattern; and
    a container for heating articles with the inductive heating coil, wherein the container comprises a bin, lid, and gasket configured to form a hermetic seal.

11. The oven of claim 10, wherein the bin is composed of aluminum, lid is composed of a transparent material, and the gasket composed of an elastomeric.

12. The oven of claim 10, further comprising a cabinet having at least one fan and an air flow switch, wherein the microcontroller is configured to energize the power supply contingent upon the air flow switch detecting air flow.

13. The oven of claim 10, further comprising a cabinet having at least one door and at least one contact closure sensor, wherein the microcontroller is configured to energize the power supply contingent upon the contact closure sensor detecting that the at least one door is closed.

14. The oven of claim 10, further comprising a cabinet having at least one proof switch, wherein the microcontroller is configured to energize the power supply contingent upon the proof switch detecting that the container is in the cabinet.

15. The oven of claim 10, wherein the inductive heating coil comprises a plurality of loops, each loop comprising a plurality of straight segments of copper that form the shape of a rectangle.

16. The oven of claim 15, wherein each of the plurality of rectangular loops is characterized by a diagonal, wherein the length of the diagonal is different for each of the plurality of loops.

17. The oven of claim 16, wherein the plurality of rectangular loops are nested within one another to form the shape of a spiral.

* * * * *